(12) United States Patent
Hseu et al.

(10) Patent No.: US 6,251,606 B1
(45) Date of Patent: Jun. 26, 2001

(54) GENE SEQUENCE AND METHOD FOR DISTINGUISHING CORDYCEPS SINENSIS

(75) Inventors: Ruey-Shyang Hseu, 3rd Floor, No. 46, Lane 212, Chien Kuo S. Rd., Section 1, Taipei (TW); Chih-Shang Chen, Taipei (TW)

(73) Assignees: Ruey-Shyang Hseu; Soon Lo, both of Taipei; Shih-Jen Wang, Yun Lin Hsian, all of (TW)

( * ) Notice: Subject to any disclaimer, the term of this patent is extended or adjusted under 35 U.S.C. 154(b) by 0 days.

(21) Appl. No.: 09/450,656

(22) Filed: Nov. 30, 1999

(51) Int. Cl.$^7$ ........................................ C12Q 1/68
(52) U.S. Cl. ........................ 435/6; 435/91.1; 435/91.2; 424/195.1; 424/254.1; 514/169
(58) Field of Search ............................ 435/6, 91.1, 91.2; 424/195.1, 254.1; 514/169

(56) References Cited

U.S. PATENT DOCUMENTS 5,582,828 * 12/1996 Lin et al. .......................... 424/195.1

* cited by examiner

*Primary Examiner*—W. Gary Jones
*Assistant Examiner*—Janell E. Taylor
(74) *Attorney, Agent, or Firm*—Birch, Stewart, Kolasch & Birch, LLP

(57) ABSTRACT

The present invention utilizes the singularity of the 18S rRNA gene sequence of the *Cordyceps sinensis* between the NS3/NS6 primer pair as the index for distinguishing the *Cordyceps sinensis* from other Cordyceps species.

3 Claims, 9 Drawing Sheets

DNA sequences between the primer pairs NS3/NS4

1 tctggtgcca gcagccgcgg taattccagc tccaatagcg tatattaaag ttgttgtggt
61 taaaaagctc gtagttgaac cttgggcctg gctggccggt ccgcctcacc gcgtgtactg
121 gtccggccgg gcctttccct ctgtggaacc ccatgccctt cactgggcgt ggcggggaaa
181 caggactttt actttgaaaa aattagagtg ctccaggcag gcctatgctc gaatacatta
241 gcatggaata atgaaatagg acgcgcggtt ctattttgtt ggtttctagg accgccgtaa
301 tgattaatag ggacagtcgg gggcatcagt attcaatggt cagaggtgaa attcttggat
361 ccattgaaga ctaactactg cgaaagcatt tgtcaaggat gttttcatta atcaggaacg
421 aaagttaggg gatcgaagac gatcagatac cgtcgtagtc ttaaccataa actatgccga
481 ctagggatcg gacgatgtta tttttgact cgttcggcac cttacgagaa atcaaagtgc
541 ttgggctcca gggggagtat ggtcgcaagg ctgaaactt DNA sequences between the primer pairs NS5/NS6

1 aataacaggt ctgtgatgcc cttagatgtt ctgggccgca cgcgcgctac actgacggag
61 ccagcgagtc ctcccttggc cggaaggccc gggtaatctt gttaaacttc gtcgtgctgg
121 ggatagagca ttgcaattat tgctcttcaa cgaggaatcc ctagtaagcg caagtcatca
181 gcttgcgttg actacgtccc tgcccttgt acacaccgcc cgtcgctact accgattgaa
241 tggctcagtg aggcgtccgg actggcccag gggggtggga aaccgccccc cagggccggg
301 aagctctcca aactcggtca tttagaggaa gtaaaagtcg taacaaggtc tccgtaggtg
361 aacctgcgga

FIG. 9

GENE SEQUENCE AND METHOD FOR DISTINGUISHING CORDYCEPS SINENSIS

BACKGROUND OF THE INVENTION

1. Field of the Invention

The present invention utilizes the singularity of the 18S rRNA gene sequence of the *Cordyceps sinensis* between the NS3/INS6 primer pair as the index for distinguishing the *Cordyceps sinensis* from other Cordyceps species.

2. Description of the Prior Art

In the literatures, the study of *Cordyceps sinensis* is only limited on species collection, description, and identification. For some *Cordyceps sinensis* with medical value, the research can only be restricted in the analysis of active ingredients metabolized therefrom for therapy purposes. However, due to the unclearness in the sexuality and the life cycle of the *Cordyceps sinensis* and the related species and due to the collection and storage difficulty, cultivating a stroma is still hard to achieve. Therefore, a clear picture in classification and a genuine relationship between the sex generation and the sexless generation can't be clearly understood so far. Such an unclearness in understanding genuine *Cordyceps sinensis* makes dangerous of wide-spreading usage upon so-called healthy *Cordyceps sinensis'* products in Chinese communities all over the world. It is quite possible that the manufacturers use fake *Cordyceps sinensis* to produce the products, or the customers have the so-called healthy products without active ingredients of the *Cordyceps sinensis*. Either of them detours a positive cycle in using the *Cordyceps sinensis* and makes less benefit from using the *Cordyceps sinensis*.

SUMMARY OF THE INVENTION

In view of lacking a standard process to identify real *Cordyceps sinensis*, the present invention introduces a new methodology of distinguishing *Cordyceps sinensis* by rRNA gene analysis. In a prior art, a 18S rRNA gene is successfully used to distinguish various fungi. Therefore, the gene analysis of the present invention also focuses on the 18S rRNA gene. Various specimens of candidate *Cordyceps sinensis* are collected at different locations and timings so that the characteristics of those candidate *Cordyceps sinenis* can be clearly observed. Further, specimens used in the present invention also include other Cordyceps, so-called *Cordyceps sinensis* reserved in some fungi centers, and candidate Cordyceps identified to be relatives of *Cordyceps sinensis* by a Gen Bank. By analyzing the data sorting from those candidate *Cordyceps sinensis*, the exclusive characteristics of a genuine *Cordyceps sinensis* can then be obtained.

According to the present invention, DNA extracts of all specimens are sent to PCR amplification of the 18S rRNA gene by well-known primer pairs as NS1(SEQ ID NO: 23)/NS2, NS3(SEQ ID NO: 24)/NS4(SEQ ID NO: 25), NS5/NS6(SEQ ID NO: 27) and NS7(SEQ ID NO: 28)/NS8 (SEQ ID NO: 29). The gene sequences of the products from the PCR amplification are then determined by an automatic sequencing device. Then, comparisons between a genuine *Cordyceps sinensis* specimen and those candidate *Cordyceps sinensis* are carried out according to gene sequences. By the gene sequences, it is found that the 18S rRNA gene sequence of the genuine *Cordyceps sinensis* between primer pair NS3/NS6 is particularly different to those observed in relative Cordyceps. Based on the target sequence, a real *Cordyceps sinensis* can be easily determined. That is, the target sequence can be used as the flag to distinguish the *Cordyceps sinensis*. Further, after the 18S rRNA gene sequence between primer pair NS3/NS6 is determined as the flag to distinguish the *Cordyceps sinensis*, any fungus can be distinguished by amplifying its DNA extract by primer pairs NS3/NS4 and NS5/NS6 to determine the related PCR reaction of its 18S rRNA gene, by locating a gene sequence upon the PCR product with respect to the target gene sequence, and by comparing the gene sequence with the target gene sequence of the genuine *Cordyceps sinensis*. Following are operational embodiments upon above specimens. In the analysis, the 18S rRNA gene sequence between primer pairs NS1/NS2 and NS&/NS8 is not listed due to its vague role in the distinguishing process.

BRIEF DESCRIPTION OF THE TABLES AND DRAWINGS

The present invention will now be specified with reference to its preferred embodiments illustrated in the Tables and drawings, in which FIG. 1 shows locations of primer pairs in the 18S rRNA genes;

Figure 4:
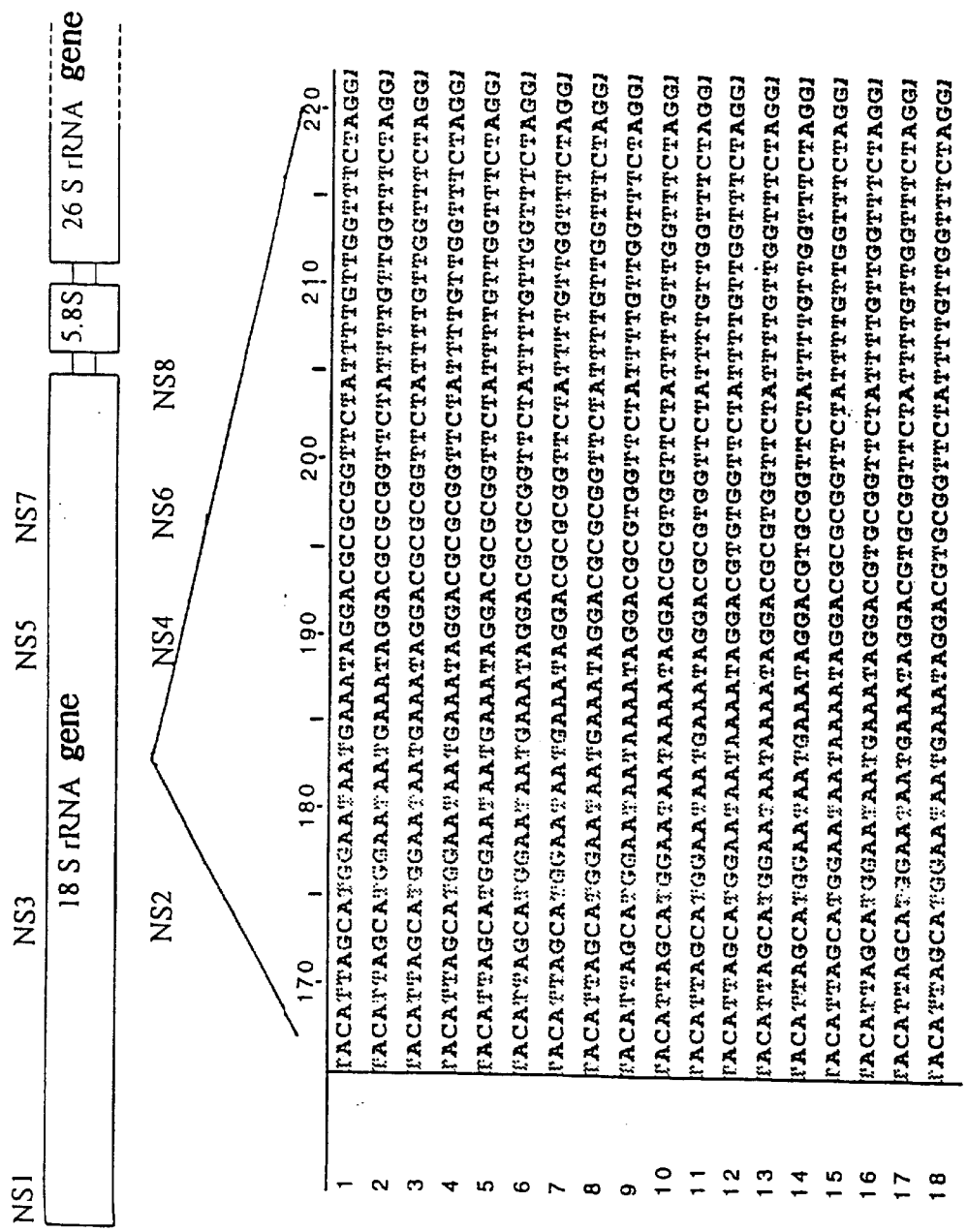
Figure 5:
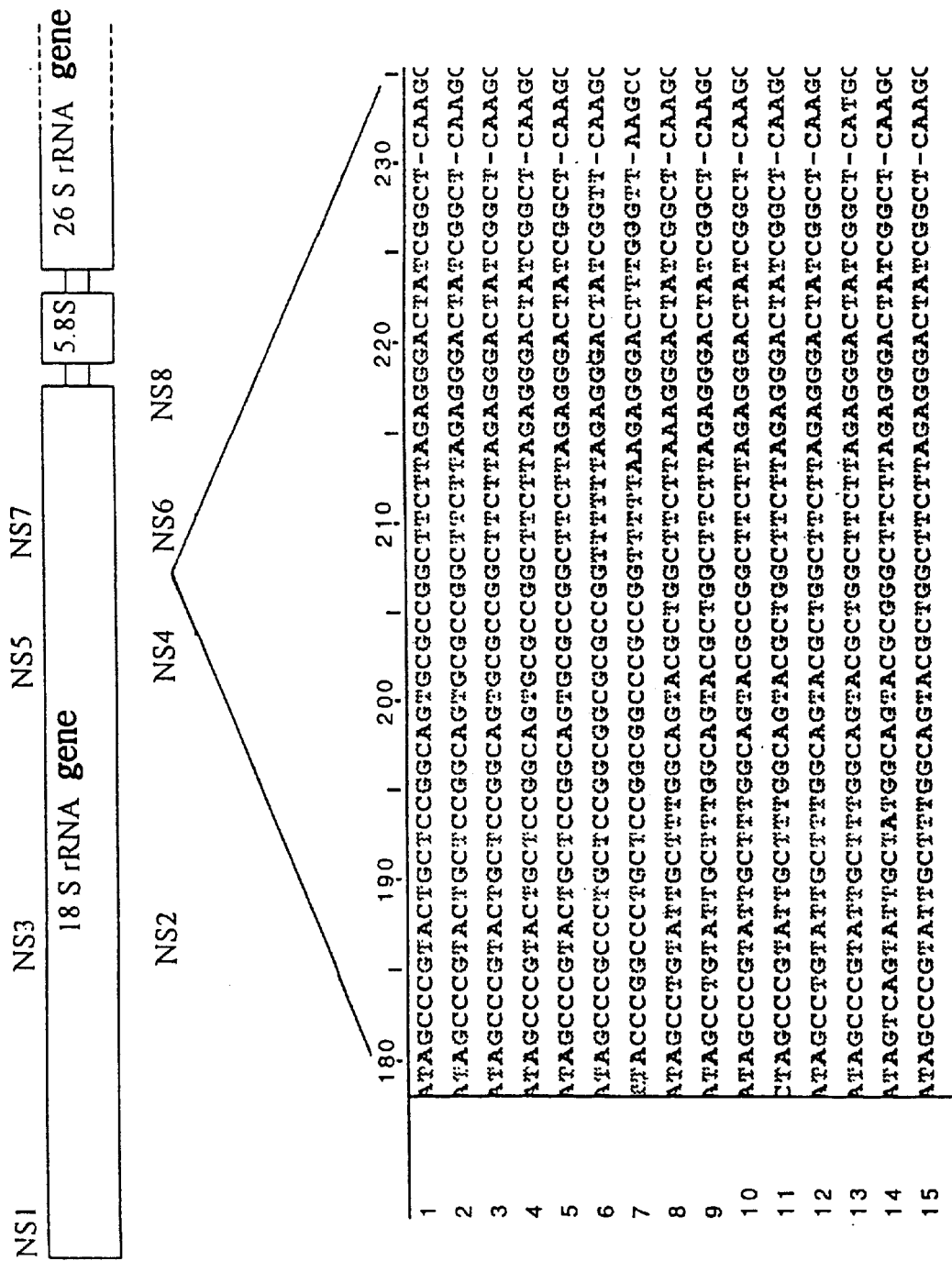
Figure 6:
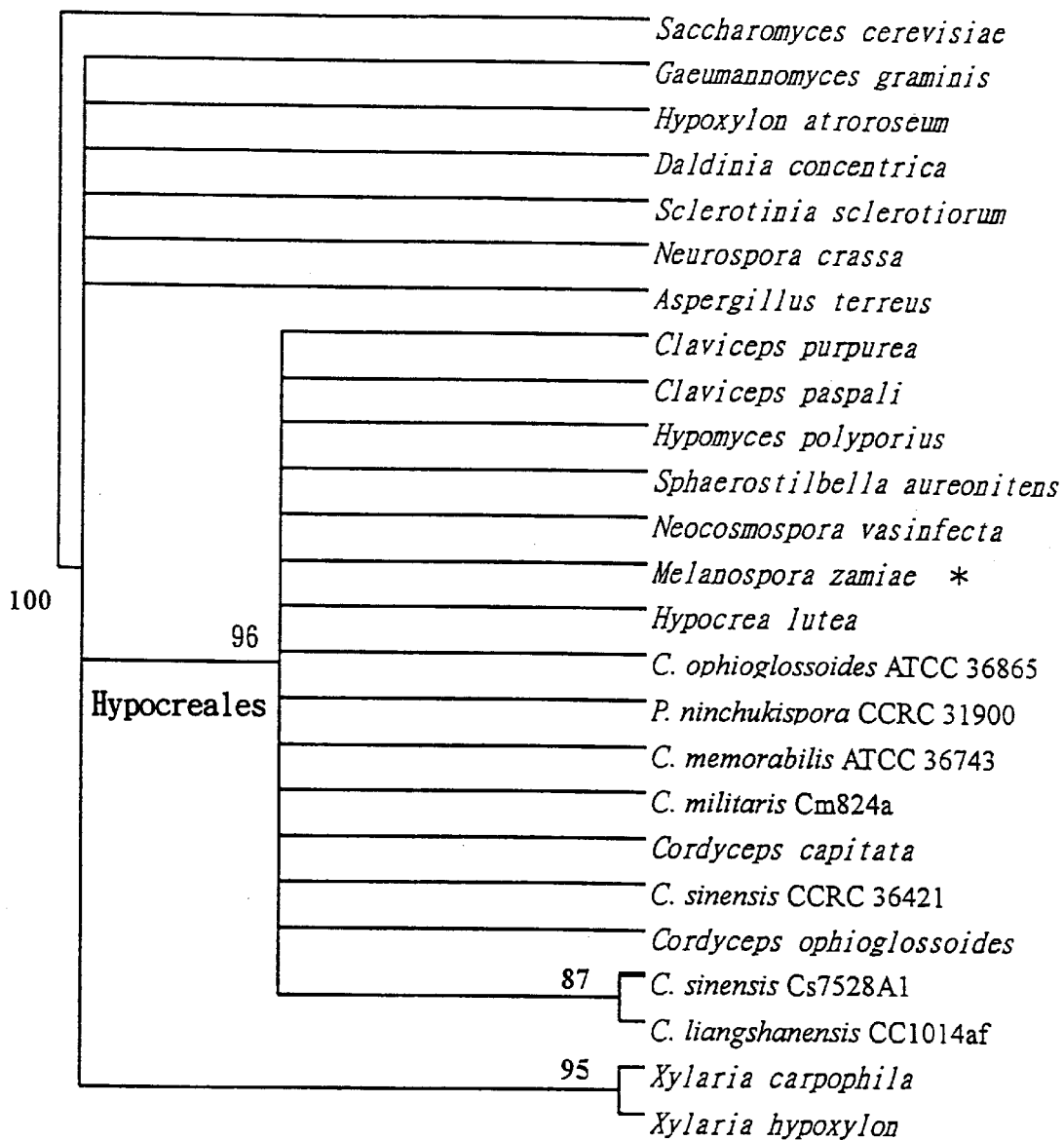
Figure 7:
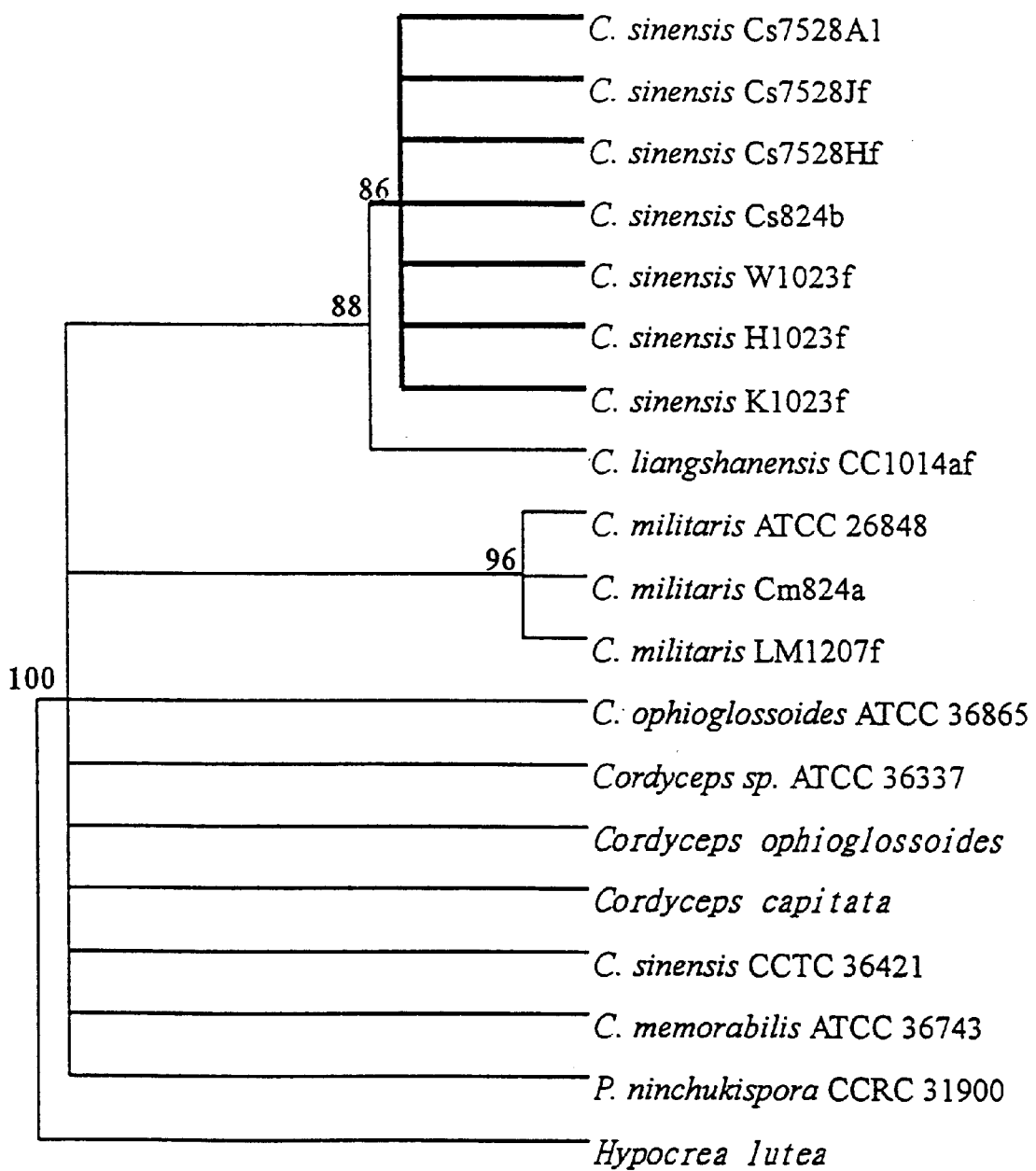
Figure 8:
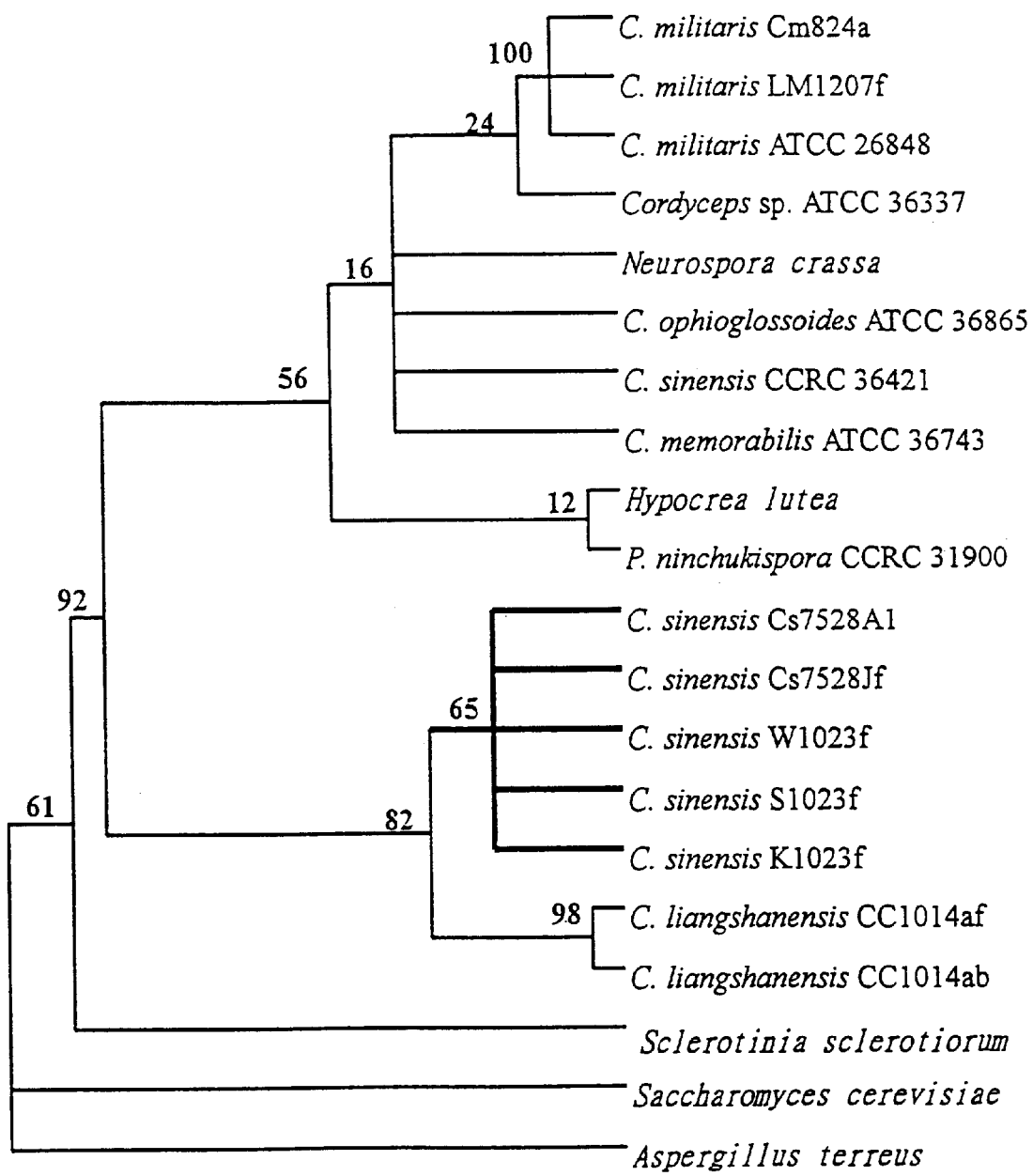

FIG. 4 shows part of 18S rRNA gene sequences (Lines 1–8, SEQ ID NO: 5; Lines 9, 10, 13, SEQ ID NO:6; Line 11, SEQ ID NO:7; Line 12, SEQ ID NO:8; Line 14, SEQ ID NO:9; Line 15, SEQ ID NO:10; Lines 16–18, SEQ ID NO:11) of Cordyceps strains between the primer pair NS3/NS4;

FIG. 5 shows part of 18S rRNA gene sequences (Lines 1–5, SEQ ID NO: 12; Line 6, SEQ ID NO:13; Line 7, SEQ ID NO:14; Line 8, SEQ ID NO:15; Line 9, SEQ ID NO:16; Line 10, SEQ ID NO:17; Line 11, SEQ ID NO:18, Line 12, SEQ ID NO:19; Line 13, SEQ ID NO:20; Line 14, SEQ ID NO:21; Line 15, SEQ ID NO:22) of Cordyceps strains between the primer pair NS5/NS6;

FIG. 6 is the phylogenetic relationship of Table 8;

FIG. 7 is the phylogenetic relationship of Table 9;

FIG. 8 is the phylogenetic relationship of Table 10; and

FIG. 9 shows the target 18S rRNA gene sequence (SEQ ID NOS; 1–2) of a genuine *Cordyceps sinensis* between the primer pair NS3/NS6.

DESCRIPTION OF THE PREFERRED EMBODIMENT

The invention disclosed herein is directed to a method for distinguishing *Cordyceps sinensis*. In the following description, numerous details are set forth in order to provide a thorough understanding of the present invention. It will be appreciated by one skilled in the art that variations of these specific details are possible while still achieving the results of the present invention. In other instances, well-known components are not described in detail in order not to unnecessarily obscure the present invention.

Figure 1:
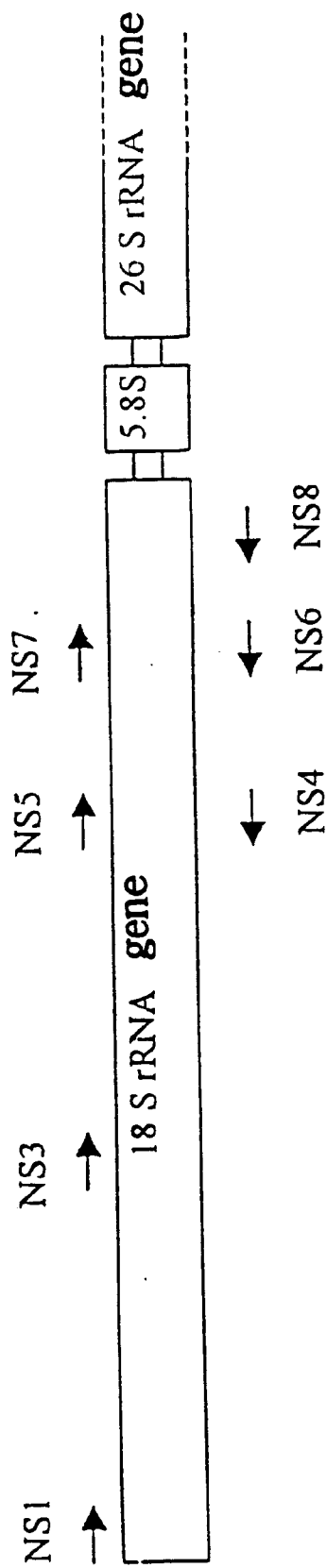

Table 1 to Table 3 list specimens of *Cordyceps sinensis*, specimens of Cordyceps and strains of Cordyceps used in the present invention. In Table 1, each specimen of *Cordyceps sinensis* is further divided into a sclerotium part and a stroma part. Thereby, the difference between the sclerotium and the stroma in the same specimen can be identified. Firstly, each specimen is cultivated for extracting DNA. The DNA is then PCR amplified separately by various primer pairs listed in Table 4 for obtaining the 18S rRNA gene. Refer to FIG. 1 for correct action positions of respective primer pairs upon 18S rRNA gene. While PCR amplifying in accordance with the present invention, the reaction conditions are 2 minutes at 98° C. for the initial denaturing temperature, 45 seconds at 95° C. for the denaturing temperature, 45 seconds at 52° C. for the annealing denaturing temperature, 35 cycles under a 2-minute 72° C. extension temperature per cycle, and finally 10 minutes at 72° C. for the final denaturing temperature. The product after PCR amplification is then gone through a high pure PCR product purification kit for purification, gene ordered by an Applied Biosystems 373 DNA sequencer, and analyzed by a tag dye deoxy terminor cycle sequencing kit. The ordered gene sequence is then reported to the European Molecular Biology Laboratory for acquiring an accession number. The corresponding accession numbers for specimens listed in Tables 1, 2, and are shown in Tables 5, 6, and 7 respectively. Primer pairs NS3, NS4 & NS5, and NS6 are recorded separately in Tables 5, 6 and 7 respectively. In Table 2, the famous *Saccharomyces cerevisiae* is already known so that no new accession numbers is recorded in Table 6.

Figure 2:
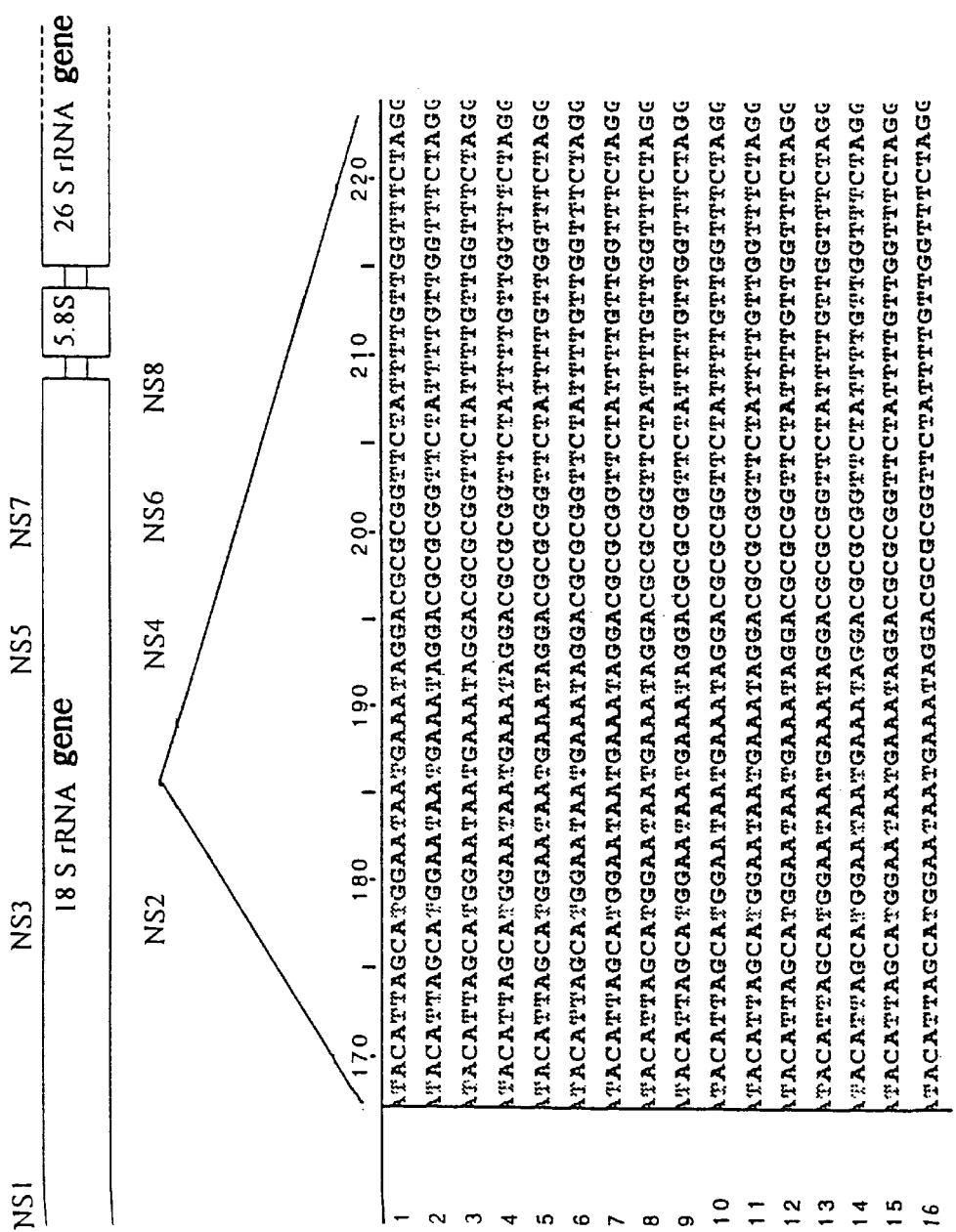
FIG. 2 shows part of 18S rRNA gene sequences (SEQ ID NO: 3) in Table 5 between the primer pair NS3/NS4.
Figure 3:
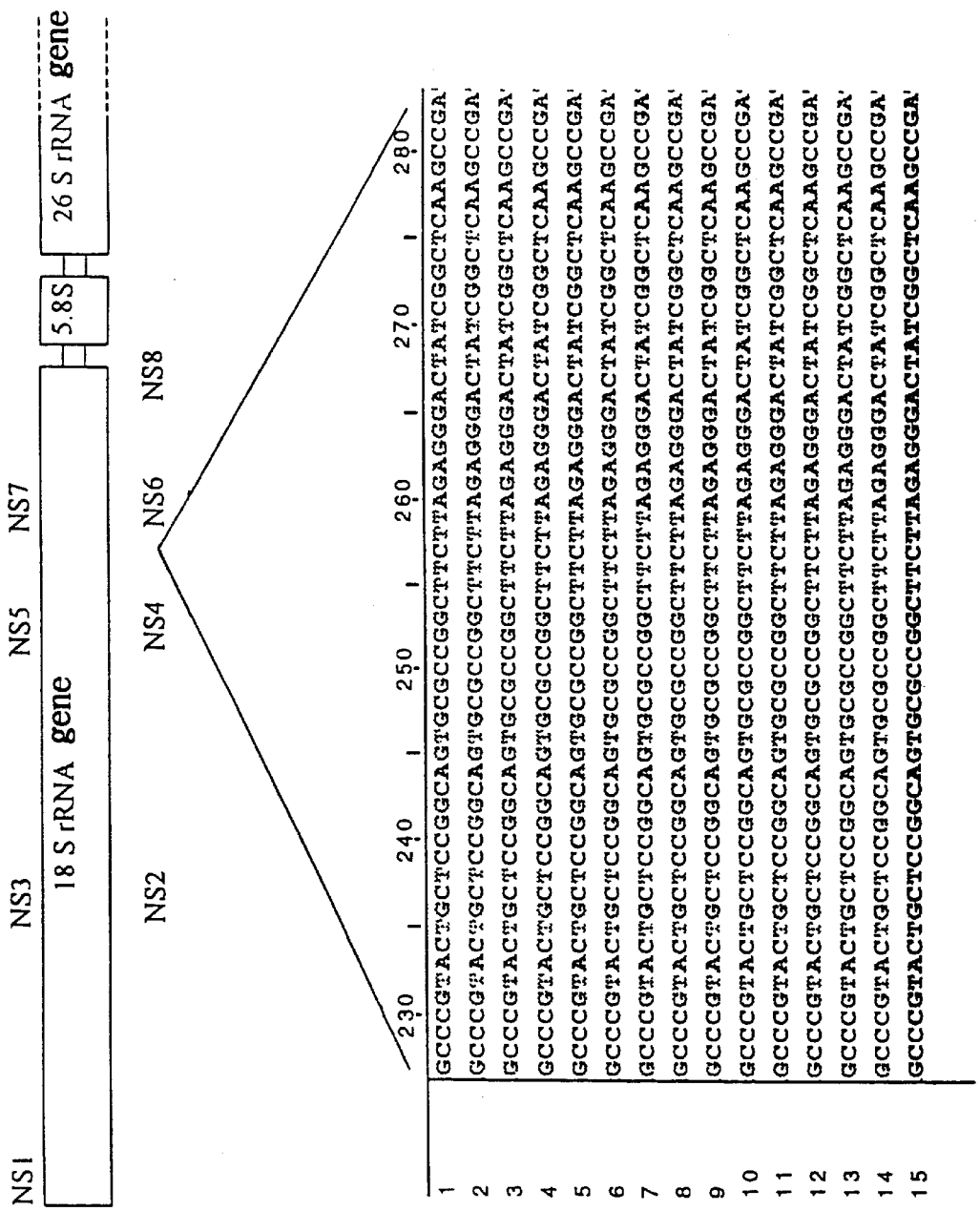
FIG. 3 shows part of 18S rRNA gene sequences (SEQ ID NO: 4)in Table 5 between the primer pair NS5/NS6.

It is obvious that the complete 18S rRNA gene sequences of a *Cordyceps sinensis* specimen are extremely long and only part of the sequences are helpful for identifying a genuine *Cordyceps sinensis*. After the analysis of the present invention, it is found that only the 18S rRNA gene sequences between the primer pairs NS3/NS4 and NS5/NS6 are valuable for the identification. FIG. 2 shows part of 18S rRNA gene sequences in Table 5 between the primer pair NS3/NS4. From columns 1 to 16 are listed specimens symbolized as Cs824af, Cs824b, W1023f, Cs7528A1, Cs7528A2, Cs7528Jf, Cs7528Jh, Cs7528Hf, Cs7528Hh, T1023f, S1023f, H1023f, K1023f, Cs1014df, Cs824ab, and Cs824ab respectively. FIG. 3 shows part of 18S rRNA gene sequences in Table 5 between the primer pair NS5/NS6. From columns 1 to 15 are listed specimens symbolized as Cs824af, Cs824ab, W1023f, Cs7528A1, Cs7528A2, Cs7528Jf, Cs7528Jh, Cs7528Hf, Cs7528Hh, T1023f, S1023f, H1023f, K1023f, Cs1014df, and Cs1014db respectively. As shown in FIG. 2 and FIG. 3, all the *Cordyceps sinensis* specimens have the same 18S rRNA gene sequences between the primer pairs NS3/NS6. It is thus proved that all these wild *Cordyceps sinensis* specimens of Table 1 are originated from the same fungi species, even the collection source and timing are different. Also, it is proved that sclerotium and the stroma of the *Cordyceps sinensis* specimen keep the same 18S rRNA gene sequences, so that they are originated from the same fungi species.

According to the present invention, the nature of the *Cordyceps sinensis* and the 18S rRNA gene sequences between the primer pairs NS3/NS6 can be observed from FIG. 2 and FIG. 3. However, it is doubtful that such evidence of gene sequences is sufficient to distinguish the genuine *Cordyceps sinensis* with other species. Further comparison upon the 18S rRNA gene sequences between the primer pairs NS3/NS6 among various specimens is still necessary. Aforesaid gene sequences are shown in FIG. 4 and FIG. 5. FIG. 4 shows part of 18S rRNA gene sequences of Cordyceps strains between the primer pair NS3/NS4, and FIG. 5 shows part of 18S rRNA gene sequences of Cordyceps strains between the primer pair NS5/NS6. From columns 1 to 18 of FIG. 4 are listed specimens symbolized as *C. Sinensis* Cs824af, Cs7528A1, Cs7528Jf, Cs7528Hh, T1023f, H1023f, *C. liangshanensis* CC1014af, *C. militaris* Cm824a, LM1207f, *P. ninchukispora* CCRC 31900, *C. memorabilis* ATCC 36743, *C. militaris* ATCC 26848, *C. ophioglossoides* ATCC 36865, *Cordyceps sp.* ATCC 36337, *C. sinensis* CCRC 36421, *C. capitata* (from Gen Bank), and *C. ophioglossoides* (from Gen Bank) respectively. From FIG. 4, difference in gene sequences between the genuine *Cordyceps sinensis* and other species can be located. Because only part of 18S rRNA gene sequences are shown in FIG. 4, gene sequences of ATCC 36337 and CCRC 36421 are similar to those of a genuine *Cordyceps sinensis*. In column 8, gene sequences of CC1014af are identical to those of a genuine *Cordyceps sinensis*. Question arises now that if the 18S rRNA gene sequences between the primer pairs NS3/NS6 can be used as a flag to identify a genuine *Cordyceps sinensis*. However, according to the observation of the present invention upon the whole gene sequences, the interested part of gene sequences have 570 base pairs. Comparing these base pairs, the ATCC 36337 has 16 base pairs different to the respective pairs of the genuine *Cordyceps sinensis*, and the CC1014af has 4 base pairs different to the respective pairs of the genuine *Cordyceps sinensis*. Therefore, even though the gene sequences can be highly coherent between the genuine *Cordyceps sinensis* with some fungi species, difference among the 18S rRNA gene sequences between the primer pairs NS3/NS4 still exists therebetween and is sufficient to distinguish a genuine *Cordyceps sinensis*.

FIG. 5 shows part of 18S rRNA gene sequences of Cordyceps strains between the primer pair NS5/NS6. From columns 1 to 15 of FIG. 5 are listed specimens symbolized as *C. Sinensis* Cs7528A1, Cs7528Jf, Cs7528Hh, S1023f, H1023f, *C. liangshanensis* CC1014af, cc1014ab, *C. militaris* Cm824a, LM1207f, *P. ninchukispora* CCRC 31900, *C. memorabilis* ATCC 36743, *C. militaris* ATCC 26848, *C. ophioglossoides* ATCC 36865, *Cordyceps sp.* ATCC 36337, and *C. sinensis* CCRC 36421 respectively. From FIG. 5, it can be observed that CC1014af and CC1014ab have most similar gene sequences with the genuine *Cordyceps sinensis*. However, among the 290 base pairs of the interested part of the 18S rRNA gene sequences between the primer pairs NS5/NS6, 14 base pairs of CC1014af and CC1014ab exist to be different to the respective base pairs of the genuine *Cordyceps sinensis*. So, difference between the genuine *Cordyceps sinensis* with some fungi species can still be told. From the gene sequences shown in FIG. 4 and FIG. 5, a conclusion can be made that the 18S rRNA gene sequences between the primer pairs NS3/NS6 do present important features suitable for being used as a flag to distinguish a genuine *Cordyceps sinensis* among fungi species.

By providing the aforesaid methodology of the present invention, a genuine *Cordyceps sinensis* can be told by judging the 18S rRNA gene sequences between the primer pairs NS3/NS6. Following will verify the species of the *Cordrceps sinensis* by analyzing the phylogenetic relationship, for furier ascertaining the application of the present invention. The analysis will focus on the relationship study of Cordyceps listed in Tables 1–3 and those in the Gen bank. As listed in Table 8, the 18S rRNA gene sequences of *Cordyceps sinensis* between the primer pairs NS3/NS6 are ordered according to the Gen bank by an Applied Biosystems 373 DNA sequencer. Then, the *S. cerevisiae* is applied as the out group to calculate the phylogenetic relationship by PAUP4.0 (Phylogenetic Analysis Using Parsimony 4.0) and the phylogenetic relationship is established by Tree View 3.0 (Diving of Environmental and Evolutionary Biology IBLS). Observed from FIG. 6, it is verified that all Hypocreales including the *Cordyceps sinensis* are unique grouped. In addition, the fungi listed in Tables 9 and 10 are also ordered and analyzed to have the phylogenetic relationships shown in FIG. 7 and FIG. 8, respectively. In FIG. 7, an *H. luta* is used as the out group to analyze the 18S rRNA gene sequences between the primer pairs NS3/NS4. On the other hand, in FIG. 8, an *A. terveus* is used as the out group to analyze the 18S rRNA gene sequences between the primer pairs NS5/NS6. As shown in FIG. 7 and FIG. 8, all the specimens of the present invention provided upon different sources and timings belong to the same group, so that a unique species is verified. Though the *C. liangshanensis* has the closer relationship with the genuine *Cordyceps sinensis*, yet small difference in between can still be told. By providing the results shown from FIG. 6 to FIG. 8, it is proved that the specimens of the present invention are all genuine *Cordyceps sinensis*, even from different sources.

According to the aforesaid description, it is further verified that the 18S rRNA gene sequences between the primer pairs NS3/NS6 shown in FIG. 9, in accordance with the present invention can be used as a flag to determine a genuine *Cordyceps sinsis*.

While the present invention has been particularly shown and described with reference to preferred embodiments, it will be understood by those skilled in the art that various changes in form and detail may be without departing from the spirit and scope of the present invention.

TABLE 1

The specimens of *Cordyceps sinensis* used in this invention.

| Species | Specimen No. | Tissue used to prepare DNA | Source | Location | Date |
|---|---|---|---|---|---|
| *Cordyceps sinensis* | Cs1014df | Stroma | | Obtained from Nantong Tonghui Edible Fungi Trading Center of Jiangsu, China | Oct. 1994 |
| *C. sinensis* | Cs1014db | Sclerotium | | Obtained from Nantong Tonghui Edible Fungi Trading Center of Jiangsu, China | Oct. 1994 |
| *C. sinensis* | Cs824af | Sclerotium | Sze Chuan, China | Purchased at Chinese drug store in Taipei | Oct. 1995 |
| *C. sinensis* | C5824ab | Sclerotium | Sze Chuan, China | Purchased at Chinese drug store in Taipei | Oct. 1995 |
| *C. sinensis* | Cs824b | Sclerotium | Sze Chuan, China | Purchased at Chinese drug store in Taipei | Oct. 1995 |
| *C. sinensis* | Cs7528A1 | Sclerotium | Tibet, China | Collected in Tibet, China | May 1997 |
| *C. sinensis* | Cs7528A2 | Stroma | Tibet, China | Collected in Tibet, China | May 1997 |
| *C. sinensis* | Cs7528Jf | Stroma | | Purchased at Chinese drug store in Taipei | May 1997 |
| *C. sinensis* | Cs7528Jh | Sclerotium (head) | | Purchased at Chinese drug store in Taipei | May 1997 |
| *C. sinensis* | Cs7528Hf | Stroma | | Purchased at Chinese drug store in Taipei | May 1997 |
| *C. sinensis* | Cs7528Hh | Sclerotium (head) | | Purchased at Chinese drug store in Beijing | May 1997 |
| *C. sinensis* | W1023f | Stroma | Sze Chuan, China | Purchased at Chinese drug store in Taipei | Sep. 1996 |
| *C. sinensis* | S1023f | Stroma | Tibet, China | Purchased at Chinese drug store in Taipei | Oct. 1998 |
| *C. sinensis* | T1023f | Stroma | Qinghai, China | Purchased at Chinese drug store in Taipei | Oct. 1998 |
| *C. sinensis* | H1023f | Stroma | Qinghai, China | Purchased at Chinese drug store in Qinghai, China | Oct. 1998 |
| *C. sinensis* | K1023f | Stroma | | Purchased at Chinese drug store in Taipei | Oct. 1998 |

TABLE 2

The Cordyceps spp. specimens and *Saccharomyces cerevisiae* used in this invention.

| Species | Specimen No. | Tissue used to prepare DNA | Source | Location | Date |
|---|---|---|---|---|---|
| *Cordyceps militaris* | Cm824a | stroma | China | purchased at Chinese drug store in Taipei | May 1997 |
| *C. militaris* | Cm1014c | stroma | China | purchased at Chinese drug store in Taipei | May 1997 |
| *C. militaris* | LM1207f | stroma | China | obtained from Sericultural Science Research Institute of Jilin, China | May 1997 |
| *C. liangshanensis* | CC1014af | stroma | China | | |

TABLE 2-continued

The Cordyceps spp. specimens and *Saccharomyces cerevisiae* used in this invention.

| Species | Specimen No. | Tissue used to prepare DNA | Source | Location | Date |
|---|---|---|---|---|---|
| *C. liangshanensis* | CC1014ab | sclerotium | China | | |
| *Saccharomyces cerevisiae* | Y824a | cells | this laboratory | purchased in Taipei | 1991 |

TABLE 3

The Cordyceps strains and reference strains used in this invention.

| Species | Collection No. | Source |
|---|---|---|
| *Cordyceps memorabilis* | ATCC 36743 | American Type Culture Collection, U.S.A. |
| *C. militaris* | ATCC 26848 | American Type Culture Collection, U.S.A. |
| *C. ophioglossoides* | ATCC 36865 | American Type Culture Collection, U.S.A. |
| Cordyceps sp. | ATCC 36337 | American Type Culture Collection, U.S.A. |
| *C. sinensis* | CCRC 36421 | Culture Collection & Research Center, Hsinchu, Taiwan. |
| *Phytocordyceps ninchukispora* (reference species) | CCRC 31900 | Culture Collection & Research Center, Hsinchu, Taiwan. |

TABLE 4

List of primers used in this invention.

| Primer designation | Primer sequences (5'→3') | Position |
|---|---|---|
| N S 1 | GTAGTCATATGCTTGTCTC | 18S rRNA gene 1–19 |
| N S 3 | GCAAGTCTGGTGCCAGCAGCC | 18S rRNA gene 553–573 |
| N S 4 | CTTCCGTCAATTCCTTTAAG | 18S rRNA gene 1131–1150 |
| N S 5 | AACTTAAAGGAATTGACGGAAG | 18S rRNA gene 1131–1148 |
| N S 6 | GCATCACAGACCTGTTATTGCCTC | 18S rRNA gene 1413–1435 |
| N S 7 | GAGGCAATAACAGGTCTGTGATGC | 18S rRNA gene 1413–1436 |
| N S 8 | TCCGCAGGTTCACCTACGGA | 18S rRNA gene 1790–1810 |

TABLE 5

The 18S rRNA gene sequence accession numbers of *Cordyceps sinensis* specimens.

| Species | Specimen No. | NS3,4 Acc. No. | NS5,6 Acc. No. |
|---|---|---|---|
| *Cordyceps sinensis* | Cs1014df | ○ | ○ |
| *C. sinensis* | Cs1014db | ○ | ○ |
| *C. sinensis* | Cs824af | AJ238505 | ○ |
| *C. sinensis* | Cs824ab | ○ | ○ |
| *C. sinensis* | Cs824b | AJ238506 | ○ |
| *C. sinensis* | Cs7528A1 | AJ009676 | AJ007566 |
| *C. sinensis* | Cs7528A2 | AJ009677 | AJ007567 |
| *C. sinensis* | Cs7528Jf | AJ009678 | AJ007568 |
| *C. sinensis* | Cs7528Th | AJ009679 | AJ007569 |
| *C. sinensis* | Cs7528Hf | AJ238504 | ○ |
| *C. sinensis* | Cs7S28Hh | AJ238689 | ○ |

TABLE 5-continued

The 18S rRNA gene sequence accession numbers of *Cordyceps sinensis* specimens.

| Species | Specimen No. | NS3,4 Acc. No. | NS5,6 Acc. No. |
|---|---|---|---|
| *C. sinensis* | W1023f | AJ238690 | ○ |
| *C. sinensis* | T1023f | AJ238691 | ○ |
| *C. sinensis* | S1023f | AJ238691 | ○ |
| *C. sinensis* | H1023f | AJ238693 | ○ |
| *C. sinensis* | K1023f | AJ238692 | ○ |

○: Pending

TABLE 6

The 18S rRNA gene sequence accession numbers of Cordyceps spp. specimens.

| Species | Specimen No. | NS3,4 Acc. No. | NS5,6 Acc. No. |
|---|---|---|---|
| *Cordyceps militaris* | Cm824a | AJ009682 | AJ007571 |
| *C. militaris* | Cm1014C | AJ009683 | AJ242435 |
| *C. militaris* | LM1207f | AJ009681 | AJ242436 |
| *C. liangshanensis* | CC1014af | AJ238503 | AJ239070 |
| *C. liangshanensis* | CC1014ab | AJ238503 | AJ239071 |

TABLE 7

The 18S rRNA gene sequence accession numbers of Cordyceps spp. strains.

| Species | Collection No. | NS3,4 Acc. No. | NS5,6 Acc. No. |
|---|---|---|---|
| Cordyceps memorabilis | ATCC 36743 | AJ238501 | AJ242432 |
| C. militaris | ATCC 26848 | AJ238500 | AJ242430 |
| C. ophioglossoides | ATCC 36865 | AJ238498 | AJ242431 |
| Cordyceps sp. | ATCC 36337 | AJ242429 | AJ242433 |
| Phytocordyceps ninchukispora | CCRC 31900 | AJ238499 | AJ242434 |
| C. sinensis | CCRC 36421 | AJ238502 | AJ239072 |
| C. sinensis | CsRSbH1 | AJ009680 | AJ067570 |
| C. sinensis | RS2 | AJ133815 | AJ242427 |
| C. sinensis | RS3 | AJ238685 | ○ |
| C. sinensis | RS4-2 | AJ238686 | ○ |
| C. sinensis | RS5-2 | AJ238687 | AJ242427 |
| C. sinensis | RS6-3 | AJ238688 | AJ242428 |
| C. sinensis | MCs1014b | AJ238496 | AJ242437 |
| C. sinensis | MCs119 | AJ238497 | ○ |

○: Pending

TABLE 8

The species and sequences accession numbers used in FIG. 6.

| Species | Accession Number | Order | Source |
|---|---|---|---|
| Cordyceps sinensis Cs7528A1 | AJ009676 | Hypocreales | inventor |
| C. sinensis CCRC 36421 | AJ238502 | Hypocreales | inventor |
| C. ophioglossoides ATCC 36865 | AJ238498 | Hypocreales | inventor |
| C. memorabilis ATCC 36743 | AJ238501 | Hypocreales | inventor |
| C. militaris ATCC 26848 | AJ009683 | Hypocreales | inventor |
| C. liangshanensis CC1014af | AJ238503 | Hypocreales | inventor |
| P. ninchukispora CCRC 31900 | AF238499 | Hypocreales | inventor |
| Saccharomyces cerevisiae | J01353 | Saccharomycetales | GenBank |
| Gaeumannomyces graminis | AF050488 | Diapothales | GenBank |
| Hypoxylon atroroseum | U32411 | Xylariales | GenBank |
| Daldinia concentrica | U47828 | Xylariales | GenBank |
| Sclerotinia sclerotiorum | X69850 | Leotiales | GenBank |
| Neurospora crassa | NCRRNAS | Sordariales | GenBank |
| Aspergillus terreus | AB008409 | Eurotiales | GenBank |
| Claviceps purpurea | U44040 | Hypocreales | GenBank |
| Claviceps paspali | U32401 | Hypocreales | GenBank |
| Hypomyces polyporius | U32410 | Hypocreales | GenBank |
| Sphaerostilbella aureonitens | U32415 | Hypocreales | GenBank |
| Neocosmospora vasinfecta | U32414 | Hypocreales | GenBank |
| Melanospora zamiae | U78356 | Melanosporales | GenBank |
| Hypocrea lutea | U00IFOC | Hypocreales | GenBank |
| Cordyceps capitata | U44041 | Hypocreales | GenBank |
| Cordyceps ophioglossoides | U46881 | Hypocreales | GenBank |
| Xylaria carpophila | Z49785 | Xylariales | GenBank |
| Xylaria hypoxhlon | U20378 | Xylariales | GenBank |

TABLE 9

The species and sequences accession numbers used in FIG. 7.

| Species | Accession Number | Source |
|---|---|---|
| Cordyceps sinensis Cs7528A1 | AJ009676 | inventor |
| C. sinensis Cs7528Jf | AJ009678 | inventor |
| C. sinensis Cs7528Hf | AJ238504 | inventor |
| C. sinensis Cs824b | AJ238506 | inventor |
| C. sinensis W1023f | AJ238690 | inventor |
| C. sinensis K1023f | AJ238692 | inventor |
| C. sinensis sisH1023f | AJ238693 | inventor |
| C. sinensis CCRC 36421 | AJ238502 | inventor |
| C. ophioglossoides ATCC 36865 | AJ238498 | inventor |
| C. memorabilis ATCC 36743 | AJ238501 | inventor |
| Cordyceps sp. ATCC 36337 | AJ242429 | inventor |
| C. militaris ATCC 26848 | AJ009683 | inventor |
| C. militaris Cm824a | AJ009682 | inventor |
| C. militaris LM1207f | AJ009681 | inventor |
| C. liangshanensis CC1014af | AJ238503 | inventor |
| P. ninchukispora CCRC 31900 | AJ238499 | inventor |
| Hypocrea lutea | U00IFOC | GenBank |
| 0 capitata | U44041 | GenBank |
| c. ophioglossoides | U46881 | GenBank |

TABLE 10

The species and sequences accession numbers used in FIG. 8.

| Species | Accession Number | Order | Source |
|---|---|---|---|
| Cordyceps sinensis Cs7528A1 | AJ007566 | Hypocreales | inventor |
| C. sinensis Cs7528Jf | AJ007568 | Hypocreales | inventor |
| C. sinensis W1023f | ○ | Hypocreales | inventor |
| C. sinensis K1023f | ○ | Hypocreales | inventor |
| C. sinensis S1023f | ○ | Hypocreales | inventor |
| C. sinensis CCRC 36421 | AJ239072 | Hypocreales | inventor |
| C. ophioglossoides ATCC 36865 | AJ242431 | Hypocreales | inventor |
| C. memorabilis ATCC 36743 | AJ242432 | Hypocreales | inventor |
| Cordyceps sp. ATCC 36337 | AJ242433 | Hypocreales | inventor |
| C. militaris ATCC 26848 | AJ242430 | Hypocreales | inventor |
| C. militaris Cm824a | AJ007571 | Hypocreales | inventor |
| C. militaris LM1207f | AJ242436 | Hypocreales | inventor |
| C. liangshanensis CC1014af | AJ239070 | Hypocreales | inventor |
| C. liangshanensis CC1014ab | AJ239071 | Hypocreales | inventor |
| P. ninchukispora CCRC 31900 | AJ242434 | Hypocreales | inventor |
| Hypocrea lutea | U00IFOC | Hypocreales | GenBank |
| Saccharomyces cerevisiae | J01353 | Saccharomycetales | GenBank |
| Sclerotinia sclerotiorum | X69850 | Leotiales | GenBank |
| Neurnspora crassa | NCRRNAS | Sordariales | GenBank |
| Aspergillus terreus | AB008409 | Eurotiales | GenBank |

○: Pending

What is claimed is:

1. Gene sequences for distinguishing *Cordyceps sinensis*, by judging a PCR-amplified 18S rRNA gene between primer pairs NS3/NS6, comprising:

the DNA sequence (SEQ ID NO: 1) between the primer pairs NS3/NS4; and the DNA sequence (SEQ ID NO: 2) between the primer pairs NS5/NS6.

2. A method for distinguishing *Cordyceps sinensis* by:

obtaining an 18S rRNA gene by PCR;

amplifying an extracted DNA from a specimen through primer pairs NS3/NS4 and NS5/NS6;

applying a DNA sequencer to order gene sequences of PCR amplified products;

and comparing the gene sequences of the PCR amplified products with the gene sequences of claims to determine whether the specimen is a genuine *Cordyceps sinensis*.

3. The method of claim 2, wherein the DNA sequencer is an Applied Biosystems 373 DNA sequencer.

\* \* \* \* \*

SEQUENCE LISTING

<160> NUMBER OF SEQ ID NOS: 29

<210> SEQ ID NO 1
<211> LENGTH: 579
<212> TYPE: DNA
<213> ORGANISM: Cordyceps sinensis

<400> SEQUENCE: 1

```
tctggtgcca gcagccgcgg taattccagc tccaatagcg tatattaaag ttgttgtggt    60
taaaaagctc gtagttgaac cttgggcctg gctggccggt ccgcctcacc gcgtgtactg   120
gtccggccgg gcctttccct ctgtggaacc ccatgccctt cactgggcgt ggcggggaaa   180
caggactttt actttgaaaa aattagagtg ctccaggcag gcctatgctc gaatacatta   240
gcatggaata atgaaatagg acgcgcggtt ctattttgtt ggtttctagg accgccgtaa   300
tgattaatag ggacagtcgg gggcatcagt attcaatggt cagaggtgaa attcttggat   360
ccattgaaga ctaactactg cgaaagcatt tgtcaaggat gttttcatta atcaggaacg   420
aaagttaggg gatcgaagac gatcagatac cgtcgtagtc ttaaccataa actatgccga   480
ctagggatcg gacgatgtta ttttttgact cgttcggcac cttacgagaa atcaaagtgc   540
ttgggctcca gggggagtat ggtcgcaagg ctgaaactt                          579
```

<210> SEQ ID NO 2
<211> LENGTH: 370
<212> TYPE: DNA
<213> ORGANISM: Cordyceps sinensis

<400> SEQUENCE: 2

```
aataacaggt ctgtgatgcc cttagatgtt ctgggccgca cgcgcgctac actgacggag    60
ccagcgagtc ctcccttggc cggaaggccc gggtaatctt gttaaacttc gtcgtgctgg   120
ggatagagca ttgcaattat tgctcttcaa cgaggaatcc ctagtaagcg caagtcatca   180
gcttgcgttg actacgtccc tgcccttttgt acacaccgcc cgtcgctact accgattgaa   240
tggctcagtg aggcgtccgg actggcccag gggggtggga aaccgccccc cagggccggg   300
aagctctcca aactcggtca tttagaggaa gtaaaagtcg taacaaggtc tccgtaggtg   360
aacctgcgga                                                          370
```

<210> SEQ ID NO 3
<211> LENGTH: 58
<212> TYPE: DNA
<213> ORGANISM: Cordyceps sinensis
<220> FEATURE:
<221> NAME/KEY: misc_feature
<222> LOCATION: (1)..(58)
<223> OTHER INFORMATION: Fig. 2 lines 1-16.

<400> SEQUENCE: 3

```
atacattagc atggaataat gaaataggac gcgcggttct attttgttgg tttctagg      58
```

<210> SEQ ID NO 4
<211> LENGTH: 57
<212> TYPE: DNA
<213> ORGANISM: Cordyceps sinensis
<220> FEATURE:
<221> NAME/KEY: misc_feature
<222> LOCATION: (1)..(57)
<223> OTHER INFORMATION: Fig. 3, lines 1-15.

<400> SEQUENCE: 4

```
gcccgtactg ctccggcagt gcgccggctt cttagaggga ctatcggctc aagccga      57

<210> SEQ ID NO 5
<211> LENGTH: 58
<212> TYPE: DNA
<213> ORGANISM: Cordyceps sinensis
<220> FEATURE:
<221> NAME/KEY: misc_feature
<222> LOCATION: (1)..(58)
<223> OTHER INFORMATION: Fig. 4, lines 1-8.

<400> SEQUENCE: 5
tacattagca tggaataatg aaataggacg cgcggttcta ttttgttggt ttctagga      58

<210> SEQ ID NO 6
<211> LENGTH: 58
<212> TYPE: DNA
<213> ORGANISM: Cordyceps militaris
<220> FEATURE:
<221> NAME/KEY: misc_feature
<222> LOCATION: (1)..(58)
<223> OTHER INFORMATION: Fig. 4, lines 9-10, 13.

<400> SEQUENCE: 6
tacattagca tggaataata aaataggacg cgtggttcta ttttgttggt ttctagga      58

<210> SEQ ID NO 7
<211> LENGTH: 58
<212> TYPE: DNA
<213> ORGANISM: Cordyceps memorabilis

<400> SEQUENCE: 7
tacattagca tggaataatg aaataggacg cgtggttcta ttttgttggt ttctagga      58

<210> SEQ ID NO 8
<211> LENGTH: 58
<212> TYPE: DNA
<213> ORGANISM: Cordyceps militaris

<400> SEQUENCE: 8
tacattagca tggaataata aaataggacg tgtggttcta ttttgttggt ttctagga      58

<210> SEQ ID NO 9
<211> LENGTH: 58
<212> TYPE: DNA
<213> ORGANISM: Cordyceps sp.

<400> SEQUENCE: 9
tacattagca tggaataatg aaataggacg tgcggttcta ttttgttggt ttctagga      58

<210> SEQ ID NO 10
<211> LENGTH: 58
<212> TYPE: DNA
<213> ORGANISM: Cordyceps sinensis

<400> SEQUENCE: 10
tacattagca tggaataata aaataggacg cgcggttcta ttttgttggt ttctagga      58

<210> SEQ ID NO 11
<211> LENGTH: 58
<212> TYPE: DNA
<213> ORGANISM: Cordyceps capitata
<220> FEATURE:
<221> NAME/KEY: misc_feature
<222> LOCATION: (1)..(58)
```

<223> OTHER INFORMATION: Fig. 4, lines 16-18.

<400> SEQUENCE: 11
tacattagca tggaataatg aaataggacg tgcggttcta ttttgttggt ttctagga        58

<210> SEQ ID NO 12
<211> LENGTH: 52
<212> TYPE: DNA
<213> ORGANISM: Cordyceps sinensis
<220> FEATURE:
<221> NAME/KEY: misc_feature
<222> LOCATION: (1)..(52)
<223> OTHER INFORMATION: Fig. 5, lines 1-5.

<400> SEQUENCE: 12
atagcccgta ctgctccggc agtgcgccgg cttcttagag ggactatcgg ct        52

<210> SEQ ID NO 13
<211> LENGTH: 52
<212> TYPE: DNA
<213> ORGANISM: Cordyceps liangshanensis

<400> SEQUENCE: 13
atagcccgcc ctgctccggc ggcgcgccgg tttttagag ggactatcgg tt        52

<210> SEQ ID NO 14
<211> LENGTH: 52
<212> TYPE: DNA
<213> ORGANISM: Cordyceps liangshanensis

<400> SEQUENCE: 14
ttacccggcc ctgctccggc ggcccgccgg tttttaagag ggactttggg tt        52

<210> SEQ ID NO 15
<211> LENGTH: 52
<212> TYPE: DNA
<213> ORGANISM: Cordyceps militaris

<400> SEQUENCE: 15
atagcctgta ttgctttggc agtacgctgg cttcttaaag ggactatcgg ct        52

<210> SEQ ID NO 16
<211> LENGTH: 52
<212> TYPE: DNA
<213> ORGANISM: Cordyceps militaris

<400> SEQUENCE: 16
atagcctgta ttgctttggc agtacgctgg cttcttagag ggactatcgg ct        52

<210> SEQ ID NO 17
<211> LENGTH: 52
<212> TYPE: DNA
<213> ORGANISM: Phytocordyceps ninchukispora

<400> SEQUENCE: 17
atagcccgta ttgctttggc agtacgccgg cttcttagag ggactatcgg ct        52

<210> SEQ ID NO 18
<211> LENGTH: 52
<212> TYPE: DNA
<213> ORGANISM: Cordyceps memorabilis

<400> SEQUENCE: 18
ctagcccgta ttgctttggc agtacgctgg cttcttagag ggactatcgg ct        52

-continued

<210> SEQ ID NO 19
<211> LENGTH: 52
<212> TYPE: DNA
<213> ORGANISM: Cordyceps militaris

<400> SEQUENCE: 19
atagcctgta ttgctttggc agtacgctgg cttcttagag ggactatcgg ct      52

<210> SEQ ID NO 20
<211> LENGTH: 52
<212> TYPE: DNA
<213> ORGANISM: Cordyceps ophioglossoides

<400> SEQUENCE: 20
atagcccgta ttgctttggc agtacgctgg cttcttagag ggactatcgg ct      52

<210> SEQ ID NO 21
<211> LENGTH: 52
<212> TYPE: DNA
<213> ORGANISM: Cordyceps sp.

<400> SEQUENCE: 21
atagtcagta ttgctatggc agtacgcggg cttcttagag ggactatcgg ct      52

<210> SEQ ID NO 22
<211> LENGTH: 52
<212> TYPE: DNA
<213> ORGANISM: Cordyceps sinensis

<400> SEQUENCE: 22
atagcccgta ttgctttggc agtacgctgg cttcttagag ggactatcgg ct      52

<210> SEQ ID NO 23
<211> LENGTH: 19
<212> TYPE: DNA
<213> ORGANISM: primer NS1

<400> SEQUENCE: 23
gtagtcatat gcttgtctc                                            19

<210> SEQ ID NO 24
<211> LENGTH: 21
<212> TYPE: DNA
<213> ORGANISM: primer NS3

<400> SEQUENCE: 24
gcaagtctgg tgccagcagc c                                         21

<210> SEQ ID NO 25
<211> LENGTH: 20
<212> TYPE: DNA
<213> ORGANISM: primer NS4

<400> SEQUENCE: 25
cttccgtcaa ttcctttaag                                           20

<210> SEQ ID NO 26
<211> LENGTH: 22
<212> TYPE: DNA
<213> ORGANISM: primer NS5

<400> SEQUENCE: 26

-continued

```
aacttaaagg aattgacgga ag                                        22

<210> SEQ ID NO 27
<211> LENGTH: 24
<212> TYPE: DNA
<213> ORGANISM: primer NS6

<400> SEQUENCE: 27
gcatcacaga cctgttattg cctc                                      24

<210> SEQ ID NO 28
<211> LENGTH: 24
<212> TYPE: DNA
<213> ORGANISM: primer NS7

<400> SEQUENCE: 28
gaggcaataa caggtctgtg atgc                                      24

<210> SEQ ID NO 29
<211> LENGTH: 20
<212> TYPE: DNA
<213> ORGANISM: primer NS8

<400> SEQUENCE: 29
tccgcaggtt cacctacgga                                           20
```